(12) United States Patent
Motooka et al.

(10) Patent No.: US 9,700,319 B2
(45) Date of Patent: Jul. 11, 2017

(54) SURGICAL STAPLING AND CUTTING APPARATUS, CLAMP MECHANISMS, SYSTEMS AND METHODS

(71) Applicant: Cardica, Inc., Redwood City, CA (US)

(72) Inventors: Cara C. H. Motooka, Sunnyvale, CA (US); Brendan M. Donohoe, Fairfax, CA (US); Bryan D. Knodel, Flagstaff, AZ (US)

(73) Assignee: Dextera Surgical Inc., Redwood City, CA (US)

( * ) Notice: Subject to any disclaimer, the term of this patent is extended or adjusted under 35 U.S.C. 154(b) by 493 days.

(21) Appl. No.: 14/278,493

(22) Filed: May 15, 2014

(65) Prior Publication Data

US 2014/0339286 A1 Nov. 20, 2014

Related U.S. Application Data

(60) Provisional application No. 61/823,656, filed on May 15, 2013.

(51) Int. Cl.
| | |
|---|---|
| *A61B 17/04* | (2006.01) |
| *A61B 17/10* | (2006.01) |
| *A61B 17/072* | (2006.01) |
| *A61B 17/00* | (2006.01) |
| *A61B 17/29* | (2006.01) |

(52) U.S. Cl.
CPC ............ *A61B 17/07207* (2013.01); *A61B 2017/00393* (2013.01); *A61B 2017/2923* (2013.01)

(58) Field of Classification Search
CPC ............ A61B 17/07207; A61B 17/068; A61B 2017/2927; A61B 2017/00398; A61B 2017/00473; A61B 2017/00367

USPC .................. 227/175.1–182.1; 606/139, 219
See application file for complete search history.

(56) References Cited

U.S. PATENT DOCUMENTS

| | | |
|---|---|---|
| 5,413,268 A | 5/1995 | Green et al. |
| 6,217,585 B1 * | 4/2001 | Houser ................. A61F 2/958 606/108 |
| 7,055,731 B2 | 6/2006 | Shelton, IV et al. |

(Continued)

OTHER PUBLICATIONS

International Search Report, PCT/US2014/038291, mailed Jan. 29, 2015.

(Continued)

*Primary Examiner* — Robert Long
(74) *Attorney, Agent, or Firm* — Vista IP Law Group, LLP

(57) ABSTRACT

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly comprises of a trigger element that can activate a drive assembly to advance a clamp drive assembly to clamp the aforementioned target tissue. The clamp drive assembly comprises of a clamp slide member to either advance the clamp drive assembly in a first direction or retreat the clamp drive assembly in a second direction. The clamp drive assembly is movably coupled to a clamp driver member. Movement of the clamp driver member operates clamping operations of a jaw assembly of the surgical stapling device.

16 Claims, 13 Drawing Sheets

(56) References Cited

U.S. PATENT DOCUMENTS

| | | | |
|---|---|---|---|
| 7,083,075 B2 | 8/2006 | Swayze et al. | |
| 7,753,250 B2 | 7/2010 | Clauson et al. | |
| 7,832,408 B2 | 11/2010 | Shelton, IV et al. | |
| 7,918,376 B1 | 4/2011 | Knodel et al. | |
| 7,963,432 B2 | 6/2011 | Knodel et al. | |
| 8,070,036 B1 | 12/2011 | Knodel | |
| 8,096,457 B1 | 1/2012 | Manoux et al. | |
| 8,272,551 B2 | 9/2012 | Knodel et al. | |
| 8,342,378 B2 | 1/2013 | Marczyk et al. | |
| 8,439,246 B1 | 5/2013 | Knodel | |
| 8,701,960 B1 | 4/2014 | Manoux et al. | |
| 8,789,738 B2 | 7/2014 | Knodel et al. | |
| 2005/0006431 A1* | 1/2005 | Shelton, IV | A61B 17/07207 227/175.1 |
| 2005/0178813 A1* | 8/2005 | Swayze | A61B 17/07207 227/176.1 |
| 2007/0114261 A1* | 5/2007 | Ortiz | A61B 17/064 227/175.1 |
| 2007/0208330 A1* | 9/2007 | Treat | A61B 18/085 606/30 |
| 2007/0238934 A1 | 10/2007 | Viswanathan | |
| 2008/0296347 A1* | 12/2008 | Shelton, IV | A61B 17/072 227/180.1 |
| 2011/0022032 A1* | 1/2011 | Zemlok | A61B 17/07207 606/1 |
| 2011/0036892 A1* | 2/2011 | Marczyk | A61B 17/07207 227/176.1 |
| 2011/0155781 A1* | 6/2011 | Swensgard | A61B 17/07207 227/176.1 |
| 2011/0278343 A1 | 11/2011 | Knodel et al. | |
| 2012/0061446 A1 | 3/2012 | Knodel et al. | |
| 2012/0080494 A1 | 4/2012 | Thompson et al. | |
| 2012/0223121 A1* | 9/2012 | Viola | A61B 17/072 227/175.1 |
| 2012/0226112 A1 | 9/2012 | Leboeuf et al. | |
| 2012/0228358 A1* | 9/2012 | Zemlok | A61B 17/072 227/176.1 |
| 2016/0058439 A1* | 3/2016 | Shelton, IV | A61B 17/068 227/176.1 |

OTHER PUBLICATIONS

Notification of Transmittal of the International Search Report and the Written Opinion of the International Searching Authority, PCT/US2014/038281, mailed Sep. 18, 2014.

\* cited by examiner

SURGICAL STAPLING AND CUTTING APPARATUS, CLAMP MECHANISMS, SYSTEMS AND METHODS

CROSS-REFERENCE TO RELATED APPLICATION(S)

The application claims priority to Provisional U.S. Patent Application No. 61/823,656, filed on May 15, 2013, which is incorporated herein by reference.

FIELD OF THE INVENTION

The present invention relates generally to medical devices, and more particularly to surgical stapling and cutting systems, such as endocutters and microcutters.

BACKGROUND

Traditionally, surgeons use sutures to close wounds and incisions, attach separate tissue structures to one another, and perform other medical or surgical functions in various surgical procedures or operations. However, proper suturing requires significant skills to perform; in particular, complex suturing procedures can be time-consuming and/or very difficult to perform effectively. Furthermore, suturing may be impractical or unfeasible in certain situations. For example, suturing may be very difficult to perform in minimally-invasive surgical procedures where suturing tools may be required to be inserted through a small opening (often referred to as an access port) to gain access into a patient's body, and then the suturing operation is performed through the small access opening with extension tools to suture the target tissue. In such minimally-invasive surgical procedures, the opening or access port to the surgical site inside the patient may not be large enough to allow effective maneuvering of suturing tools to perform the suturing procedure efficiently and effectively. If access ports were made larger to allow for easier suturing operations, the benefits of minimally-invasive surgery, however, may be significantly reduced or altogether eliminated. Indeed, as surgical technology continues to progress, the size of the access ports required to access surgical sites in the body to perform minimally-invasive procedures correspondingly continues to decrease. Presently, micro-laparoscopy typically utilizes instruments with diameter of about 3 millimeters to about 2 millimeters to perform complex operations; e.g., laparoscopic cholecystectomy and inguinal hernia repair, etc. When instruments of such small diameters are used, the size of the access ports may also be very small. It is common that the access ports can be as small as about 3 millimeters to about 2 millimeters in diameters. The benefits of these advances in surgical technology to the patients are obvious, minimally-invasive procedures can cause less physical trauma to the patient. As such, these minimally-invasive procedures can be performed to greater percentage of patients even if they are not in the best physical condition. In addition, because there is generally less physical trauma involved, the patients may experience less discomfort, the recovery time is typically reduced, and there may be less scarring at the operation site. However, because of restricted access, it can be significantly difficult or nearly impossible sometimes to perform effective manual suturing within a patient's body through these small access ports in minimally-invasive procedures. As such, alternatives to suturing or manual suturing are highly desired.

SUMMARY OF THE INVENTION

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The handle assembly includes a trigger member to activate a clamp drive assembly to drive a clamp assembly to cause the jaw assembly to perform various clamping operations. The clamp assembly includes a clamp slide member to either advance the clamp assembly in a first direction or retreat the clamp assembly in a second direction. A clamp driver is movably coupled to the clamp assembly, wherein movement of the clamp driver causes the jaw assembly to clamp or un-clamp.

A surgical stapling device is configured for use in open and/or laparoscopic surgical procedures. The device includes a handle assembly, a shaft assembly coupled to the handle assembly, and an end-effector coupled to the shaft assembly. The end-effector comprises of a jaw assembly configured to clamp, staple, and/or cut a target tissue. The surgical stapling device also includes a mode switch member to selectively place the device in a clamping mode to operate a clamp drive assembly. The clamp drive assembly is configured to drive a clamp assembly to operate the surgical stapling device. The clamp assembly includes a slide member to either advance the clamp assembly in a first direction or retreat the clamp assembly in a second direction. A clamp driver member is movably coupled to the clamp assembly, wherein movement of the clamp driver causes a jaw assembly of the surgical stapling device to execute clamp or un-clamp operations.

A method of treating tissue with a surgical stapling device. The method includes setting a mode switch member to select a clamp drive assembly to place the surgical stapling device in a clamp mode. The method includes the steps of activating a trigger member to drive the clamp drive assembly, advancing a clamp slide member of a clamp assembly, causing displacement or movement of a clamp driver member, placing the clamp assembly in a first clamp lock feature in a clamp lock member, and placing the clamp driver member in a second clamp lock feature of the clamp lock member to set the surgical stapling device in a clamp mode. The method further includes the steps of activating a reset switch member, causing a swing arm member to engage and reset the claim lock member, releasing the clamp assembly from the first clamp lock feature of the clamp lock member, releasing the clamp driver member from the second clamp lock feature of the clamp lock member, and releasing the surgical stapling device from the clamp mode.

BRIEF DESCRIPTION OF THE DRAWINGS

The present invention will be readily understood by the following detailed description, taken in conjunction with accompanying drawings, illustrating by way of examples of the invention. The figures are merely exemplary and not limiting. The objects and elements in the drawings are not necessarily drawn to scale, proportion, precise orientation or positional relationships; instead, emphasis is focused on illustrating the principles of the invention. Descriptive terms such as "upper," "lower," "upward," "downward", "forward", "backward", and the like are intended for the convenience of the reader and refer to the orientation and/or motion of parts as illustrated and described; they do not necessarily limit the orientation or operation of the features, aspects, or embodiments of the invention. The drawings illustrate the design and utility of various features, aspects, or embodiments of the present invention, in which like element are referred to by like reference symbols or numerals. The drawings, however, depict the features, aspects, or embodiments of the invention, and should not be taken as limiting in their scope. With this understanding, the features, aspects, or embodiments of the invention will be described and explained with specificity and details through the use of the accompanying drawings in which.

As can be appropriated, the use of same or similar symbols or numerals in different figures indicates similar or identical items or features.

DETAILED DESCRIPTION

Figure 1A:
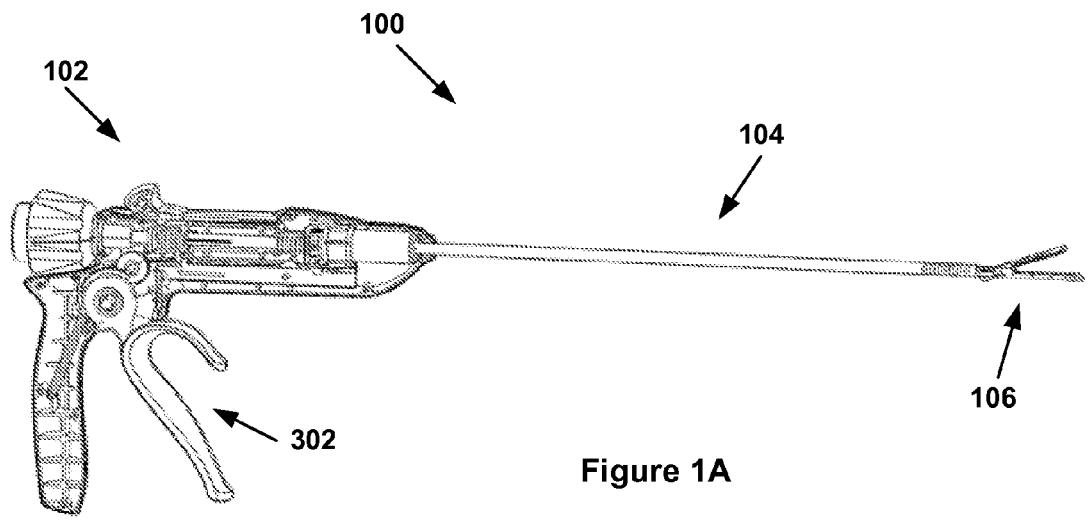
FIG. 1A and FIG. 1B illustrate an example of a surgical stapling and cutting device where the clamp mechanisms in accordance with features, aspects, or embodiments of the present invention that may be used to clamp a target tissue at a surgical site.

In the following detailed description, specific details are set forth in order to provide a thorough understanding of the present invention. However, it will be readily understood by those skilled in the art that the present invention may be practiced without these specific details. Alternatively, some of the well-known parts, component, hardware, methods of operations, and procedures may not be described in detail or elaborated so as to avoid obscuring the present invention; but, nevertheless, they are within the spirit and scope of the present invention.

As mentioned, surgeons use sutures to close wounds and incisions, attach separate tissue structures to one another, and perform other medical or surgical functions in various surgical procedures or operations. However, proper suturing requires significant skills to perform; in particular, complex suturing procedures can be time-consuming and/or very difficult to perform effectively. Furthermore, suturing may be impractical or unfeasible in certain situations. For example, suturing may be very difficult to perform in minimally-invasive surgical procedures where suturing tools may be required to be inserted through a small opening (often referred to as an access port) to gain access into a patient's body, and then the suturing operation is performed through the small access opening with extension tools to suture the target tissue. In such minimally-invasive surgical procedures, the opening or access port to the surgical site inside the patient may not be large enough to allow effective maneuvering of suturing tools to perform the suturing procedure efficiently and effectively. If access ports were made larger to allow for easier suturing operations, the benefits of minimally-invasive surgery, however, may be significantly reduced or altogether eliminated. Indeed, as surgical technology continues to progress, the size of the access ports required to access surgical sites in the body to perform minimally-invasive procedures correspondingly continues to decrease. Presently, micro-laparoscopy typically utilizes instruments with diameter of about 3 millimeters to about 2 millimeters to perform complex operations; e.g., laparoscopic cholecystectomy and inguinal hernia repair, etc. When instruments of such small diameters are used, the size of the access ports may also be very small. It is common that the access ports can be as small as about 3 millimeters to about 2 millimeters in diameters. The benefits of these advances in surgical technology to the patients are obvious, minimally-invasive procedures can cause less physical trauma to the patient. As such, these minimally-invasive procedures can be performed to greater percentage of patients even if they are not in the best physical condition. In addition, because there is generally less physical trauma involved, the patients may experience less discomfort, the recovery time is typically reduced, and there may be less scarring at the operation site. However, because of restricted access, it can be significantly difficult or nearly impossible sometimes to perform effective manual suturing within a patient's body through these small access ports in minimally-invasive procedures.

Figure 1B:
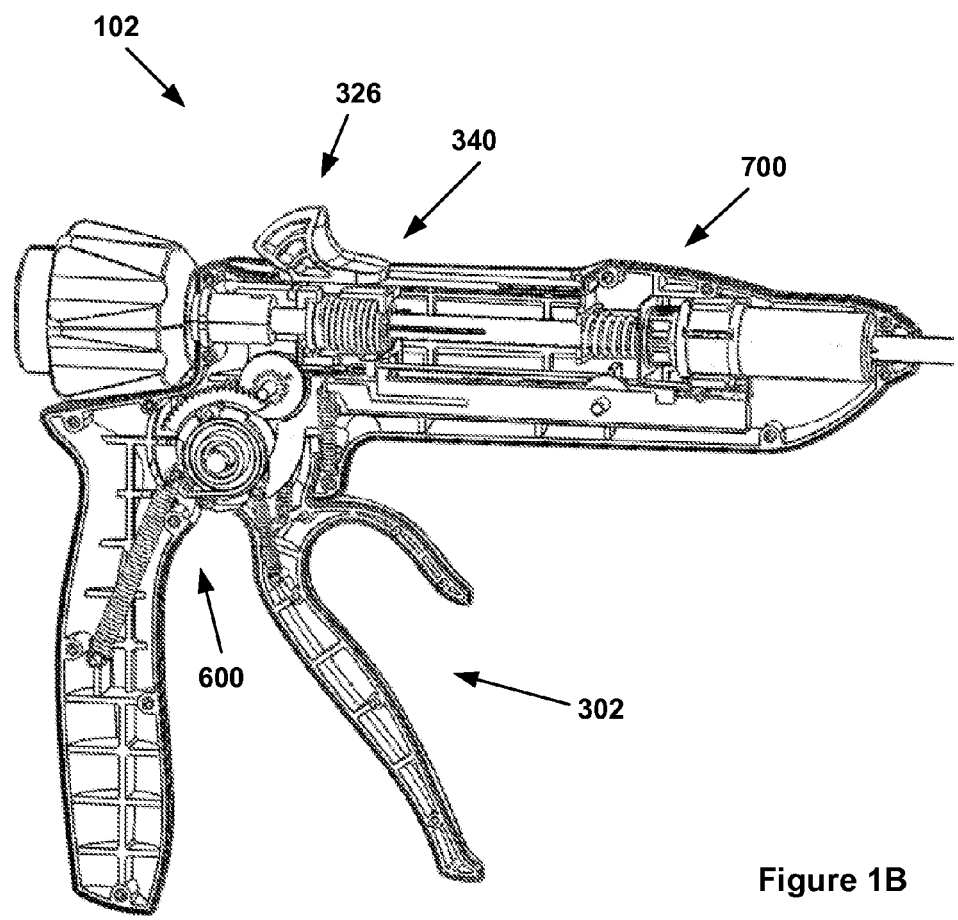

FIG. 1A and FIG. 1B illustrate an example of a surgical stapling and cutting device 100 that can be an alternative or replacement to suturing. In particular, this example of surgical stapling and cutting device 100 is especially useful for replacing suturing in minimally-invasive surgical procedures. Similarly, it can also be used in open surgeries. While this example of surgical stapling and cutting device is designed and constructed to perform stapling and cutting of tissue, the design and construction can easily be altered to include more or less functions. For example, the design and construction can be altered to perform stapling function without cutting of tissue (e.g., a knife element can be removed and/or replaced or modified so as not to include a sharp edge for cutting). As illustrated in the figures, the operation of stapling and cutting is performed through a long slim shaft 104 and a similarly slim end-effector 106. The actual operations of clamping, stapling, and cutting of tissue are performed at the distal-end 106 of the shaft 104. Further illustrated, a portion of the shaft 104 at the distal-end may be substantially flexible and may be articulated. Various versions of the endo-cutter or micro-cutter stapling systems may have non-articulated rigid shafts, while other versions may include substantially flexible or flexible portions that can be articulated. These and other features allow such examples of surgical stapling and cutting devices (e.g., MICROCUTTER XPRESS™ and MICROCUTTER XCHANGE™, which are designed and manufactured by Cardica Inc. of U.S.A.) to be ideally suited as alternatives or replacements to suturing. Greater detailed discussions of surgical stapling and cutting systems are described in U.S. patent application Ser. No. 12/323,309, filed on Nov. 25, 2008; U.S. patent application Ser. No. 12/400,760, filed on Mar. 9, 2009; U.S. patent application Ser. No. 12/400,790, filed on Mar. 9, 2009; U.S. patent application Ser. No. 12/477,065, filed on Jun. 2, 2009; U.S. patent application Ser. No. 12/787,708, filed on May 26, 2010; U.S. patent application Ser. No. 13/093,791, filed on Apr. 25, 2011; U.S. patent application Ser. No. 12/477,302, filed on Jun. 3, 2009;

U.S. patent application Ser. No. 12/489,397, filed on Jun. 22, 2009; U.S. patent application Ser. No. 12/612,614, filed on Nov. 4, 2009; U.S. patent application Ser. No. 12/840,156, filed on Jun. 20, 2010; U.S. patent application Ser. No. 13/028,148, filed on Feb. 15, 2011; U.S. patent application Ser. No. 13/048,674, filed on Mar. 15, 2011; U.S. patent application Ser. No. 13/094,716, filed on Apr. 26, 2011; U.S. patent application Ser. No. 13/094,805, filed on Apr. 26, 2011; U.S. patent application Ser. No. 13/093,743, filed on Apr. 25, 2011; U.S. patent application Ser. No. 13/105,799, filed on May 11, 2011; and U.S. patent application Ser. No. 13/294,160, filed on Nov. 10, 2011, all of which are incorporated herein by reference.

Figure 1C:
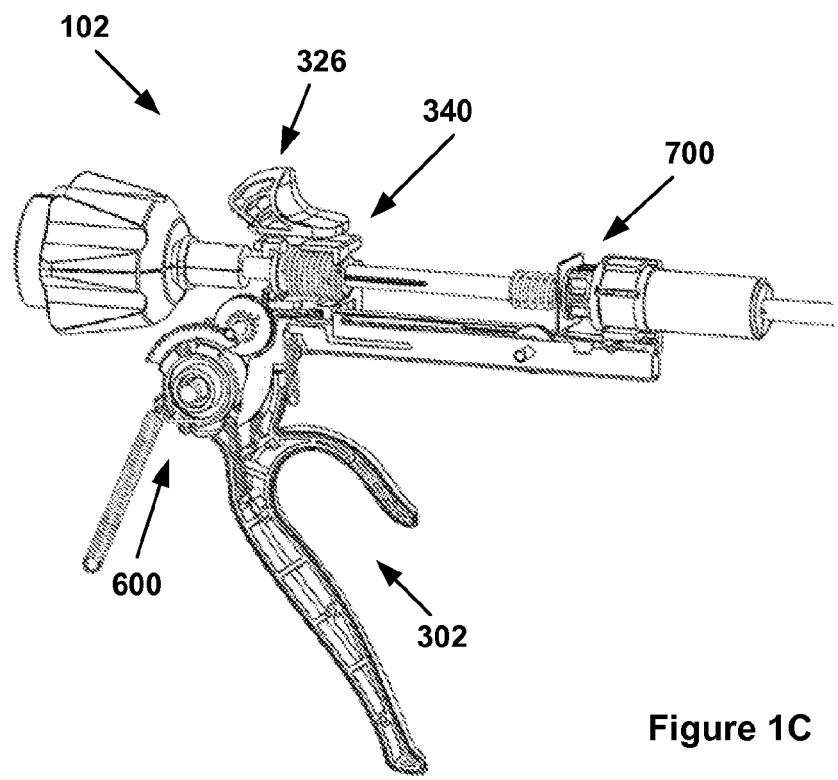
FIG. 1C through FIG. 1E illustrate closer views of the clamp mechanisms in accordance with features, aspects, or embodiments of the present invention that may be used to clamp a target tissue at a surgical site.
Figure 1D:
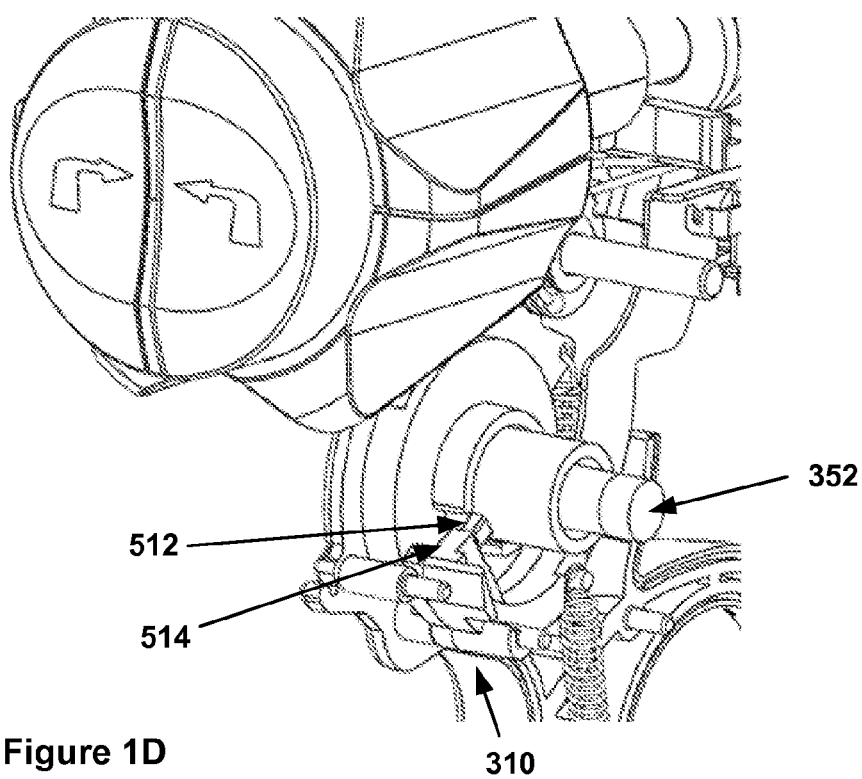
Figure 1E:
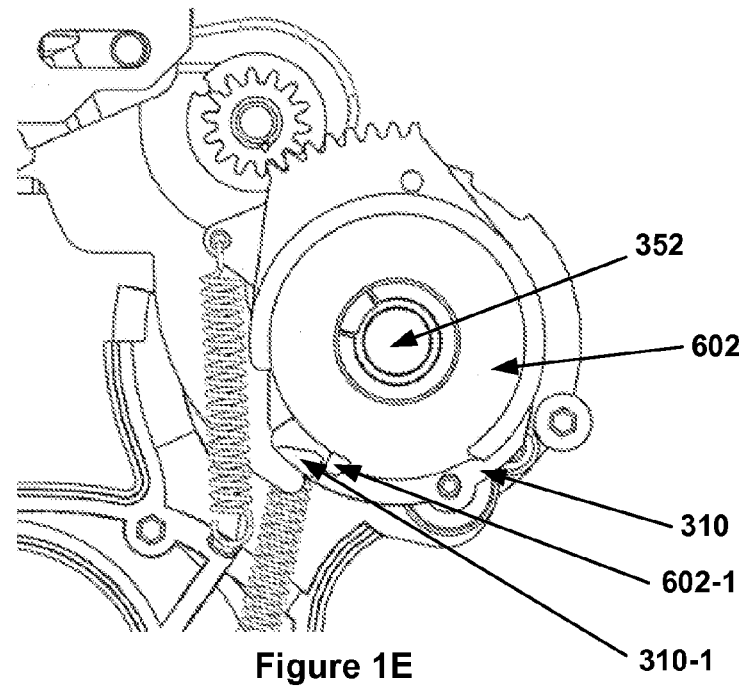

Still referring to FIG. 1A and FIG. 1B, the surgical stapling and cutting device 100 includes a handle assembly 102 with a trigger element 302, a shaft assembly 104 coupled to the handle assembly 102, and an end-effector 106 coupled to the shaft assembly 104. FIG. 1B illustrates an exposed close-up view of the handle assembly 102. In this exposed view, some of the clamp and deployment components are readily discernible. For example, the clamp drive assembly 600, clamp assembly 700, deployment assembly 340, and reset switch member 326 are all readily discernible in the exposed view of FIG. 1B. As illustrated, the handle assembly 102 comprises of a clamp drive assembly 600 that includes various gears, pulleys, springs, drive links (e.g., cables, belts, or the like), trigger elements (e.g., trigger member 302), and mode selection switch members (e.g., mode switch member 352) to operate the clamp assembly 700 and deployment assembly 340. FIG. 1C illustrates an isolated view of the handle assembly 102 which comprises of drive mechanisms 600 that includes various gears, pulleys, springs, drive links (e.g., cables, belts, or the like), trigger elements (e.g., trigger member 302), and mode selection switch members (e.g., mode switch member 352) to operate the clamp assembly 700 and deployment assembly 340. FIG. 1C illustrates the handle assembly 102 without the cover or housing so as to highlight the clamp drive mechanisms 600, the deployment assembly 340, and clamp assembly 700. FIG. 1D illustrates selection of a mode switch member 352 by engagement or disengagement of the mode switch member standoff element 512 with the ratchet member standoff element 514. Depending on the selection of the mode switch member 352, a ratchet member 310 will either engage the drive mechanisms for the deployment assembly 340 or the drive mechanisms 600 for the clamp assembly 700. The details of this disclosure will focus on the selection of the mode switch member 352 being selected to engage and/or activate the drive mechanisms of the clamp drive assembly 600 for the operation of the clamp assembly 700. When the mode switch member 352 is selected to engage or activate the drive assembly 600 for the operation of the clamp assembly 700, the ratchet member 310 engages with a first gear member 602 of the clamp drive assembly 600. The engagement may involve a drive-tooth element 310-1 of the ratchet member 310 engaging with a drive-tooth element 602-1 of the first gear 602 of the clamp drive assembly 600, as illustrated in FIG. 1E.

Figure 2A:
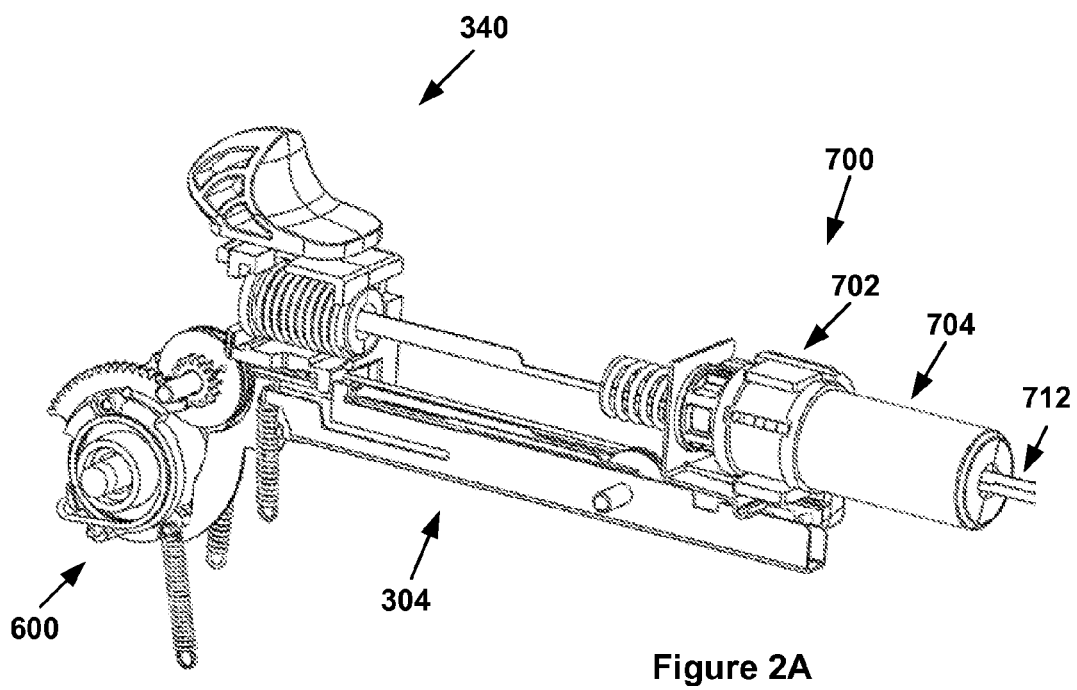
FIG. 2A through FIG. 2C illustrate the clamp mechanisms and the end-effector of the surgical stapling and cutting device at their initial neutral unclamp state.
Figure 2B:
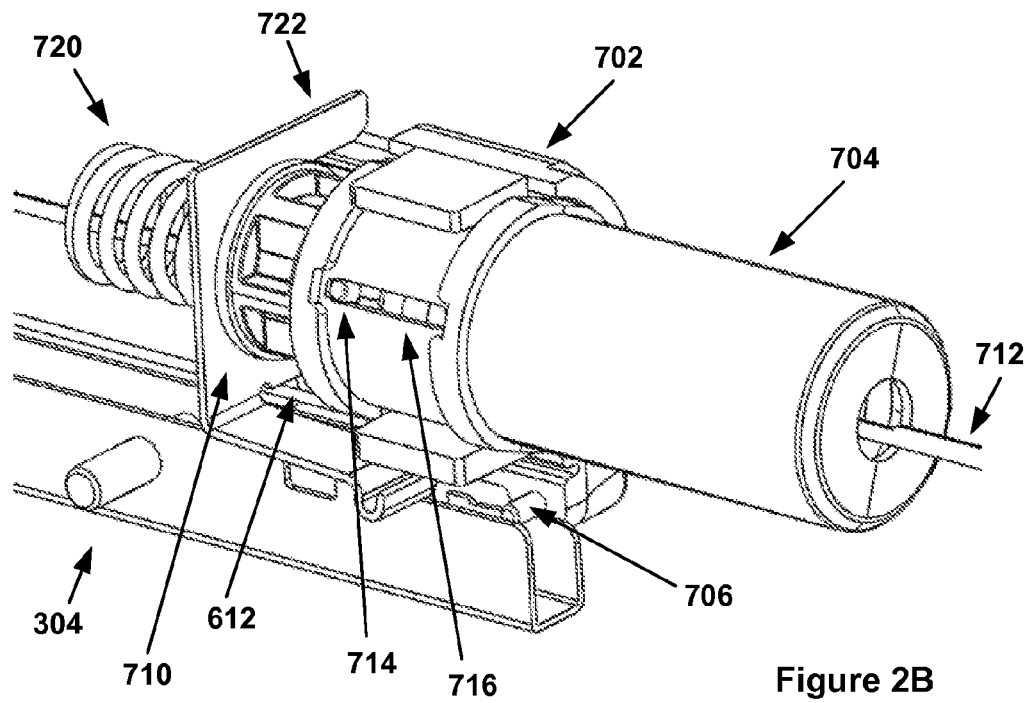
Figure 2C:
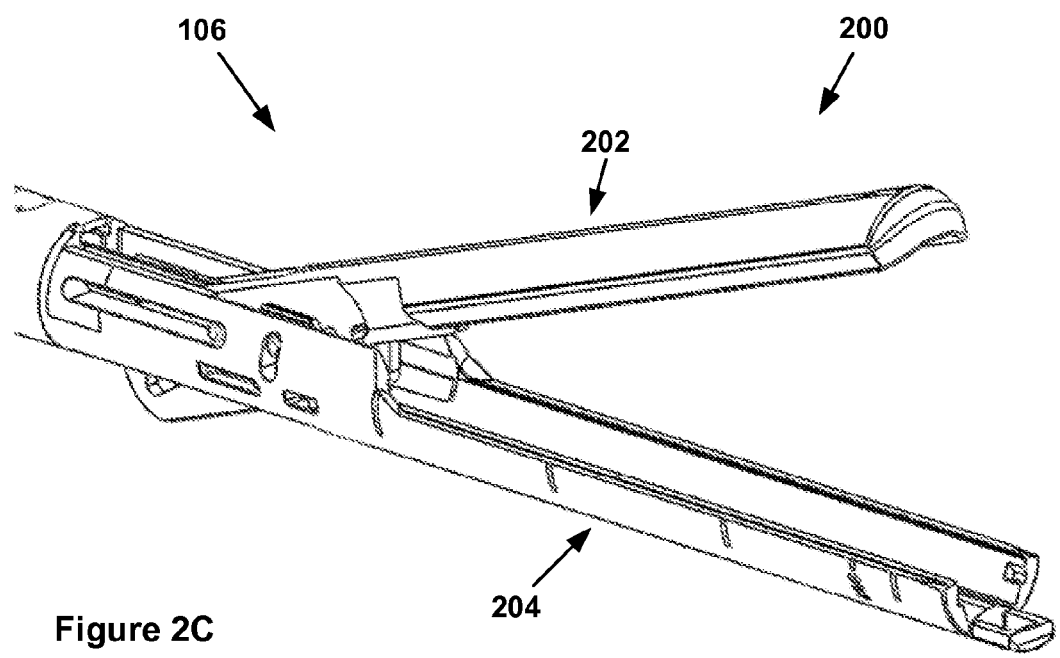

FIG. 2A through FIG. 2C illustrate the clamp mechanisms 700 and the end-effector 106 of the surgical stapling and cutting device 100 at their initial or neutral unclamp state. At the start of the clamp operational cycle, the surgical device 100 starts at a neutral unclamp state for its jaw assembly 200, see FIG. 2C. In the neutral unclamp state, the jaw members of the end-effector 106 are in their open positions. The jaw members of the end-effector 106 comprise of an anvil member 202 and a staple channel member or staple cartridge holder member 204, as illustrated in FIG. 2C. The staple channel member or staple cartridge holder member 204 is configured for holding or retaining a staple cartridge where staples may be deployed to staple target tissues. As discussed in this disclosure, a knife member may be included in the construction of the surgical device 100 or a knife member may not be included or that it may be replaced with a non-cutting member. As such, the surgical device 100 may be a surgical stapling and cutting device or it may be only a surgical stapling device depending on various options of constructions.

To place the surgical device 100 into operation, clamp mode selection may be activated through the mode switch member 352 to engage the clamp drive assembly 600, refer to FIG. 2A. A trigger element 302 may be activated (e.g., the attending surgeon may provide an initial first squeeze of the trigger element 302 of the surgical device 100). This activation of the trigger element 302 starts the clamp drive assembly 600. The drive mechanisms of the drive assembly 600 "pull" on the clamp cable member 612 which draws the clamp slide member 702 and clamp spool cover member 704 "backward" toward the proximal portion of the handle assembly 102, refer to FIG. 2B. A clamp slide pin member 706 of the clamp slide member 702 rides along a first edge or first support of the clamp lock member 304. The first edge of the clamp lock member 304 includes a ramp feature 304-1 (see FIG. 3B) that may resist the "backward" movement of the slide pin 706, which translates to providing positive feedback or resistance to the attending surgeon who is operating the trigger element 302 of the surgical device 100. The backward movement of the clamp slide member 702 and the clamp spool cover member 704 applies a compressive force onto a clamp limit member 708 (see FIG. 4B—the clamp limit member 708 may be a spring element), which translates the compressive force to the clamp driver member 710. The clamp driver member 710 is coupled to a clamp strip member 712 by way of a clamp connection bar member 714. To be discussed further, the clamp connection bar member 714 may translate laterally about a substantially lateral opening or slot 716 on the clamp slide member 702, which allows the clamp slide member 702 to be decoupled with the clamp driver member 710, see FIG. 2B.

Figure 3A:
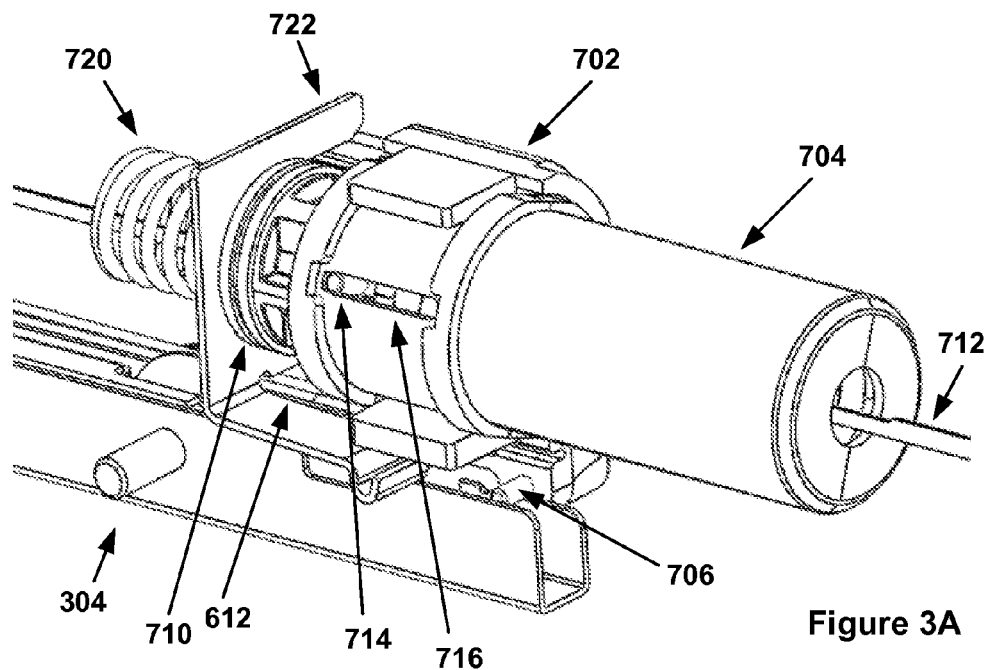
FIG. 3A through FIG. 3C illustrate the clamp mechanisms and the end-effector of the surgical stapling and cutting device at their activated trocar state.
Figure 3B:
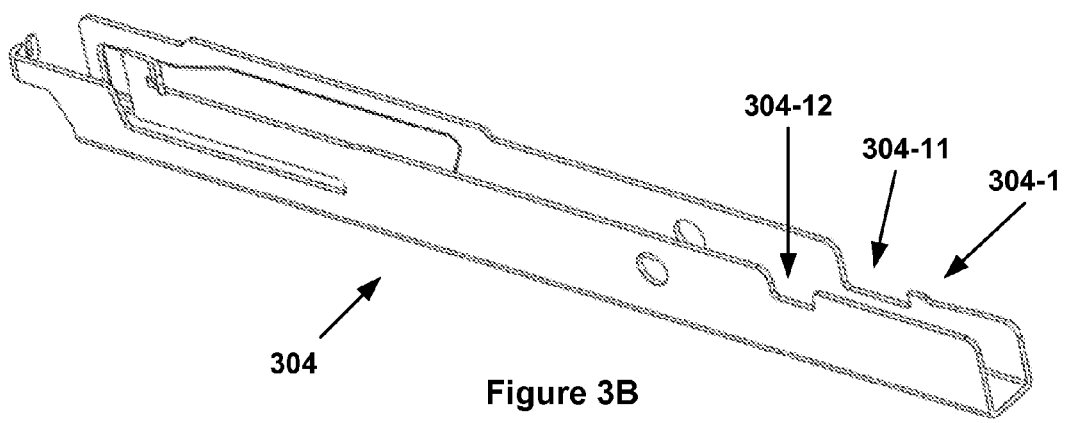
Figure 3C:
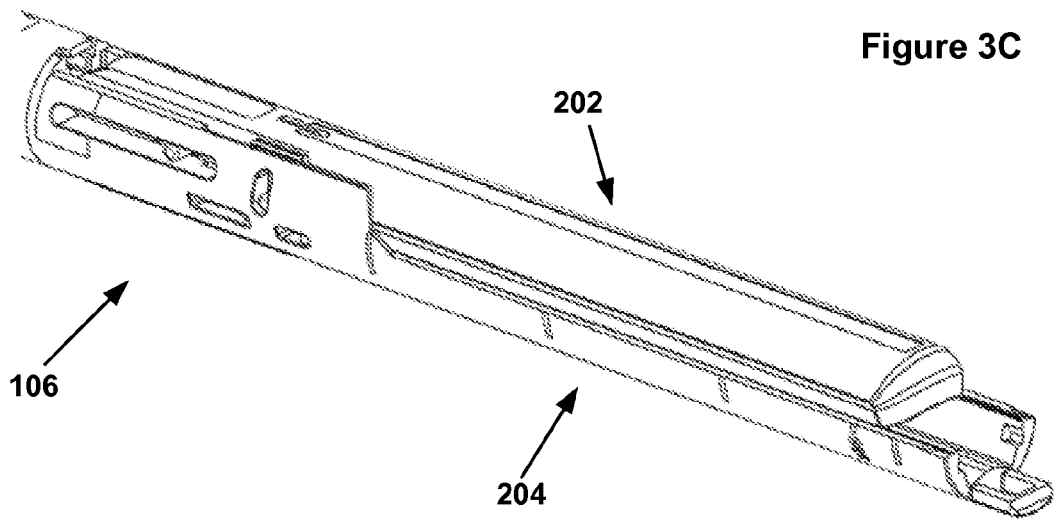
Figure 4A:
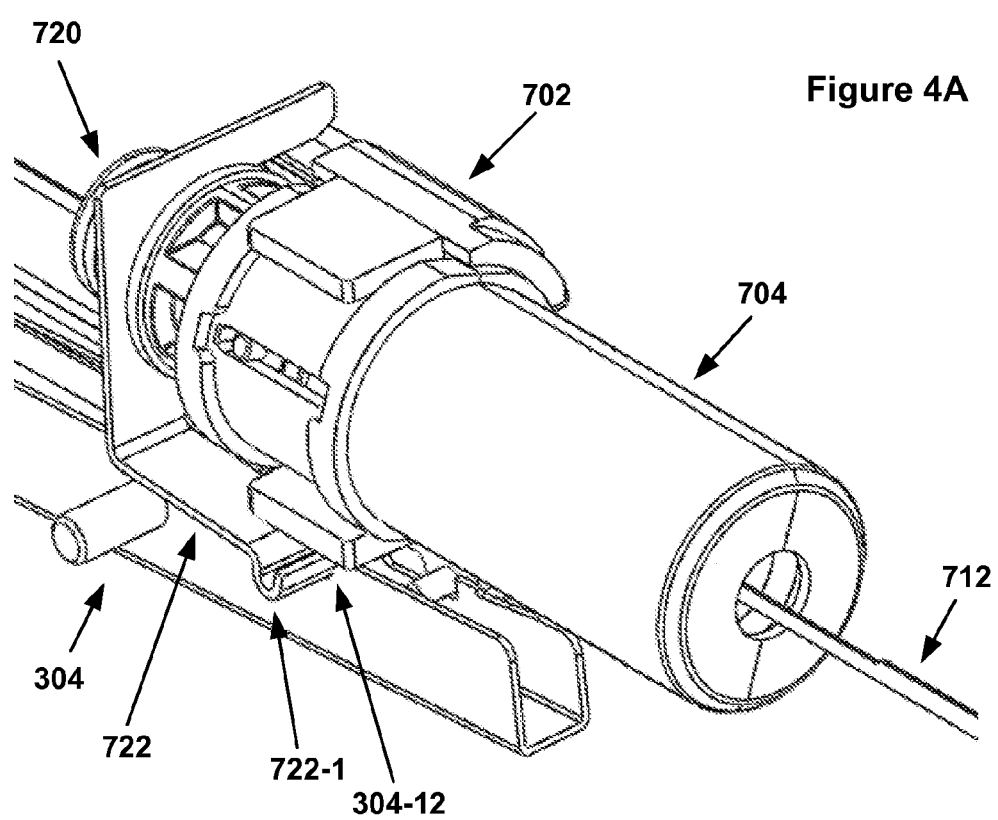
FIG. 4A through FIG. 4F illustrate the clamp mechanisms and the end-effector of the surgical stapling and cutting device at their activated clamp state.
Figure 4B:
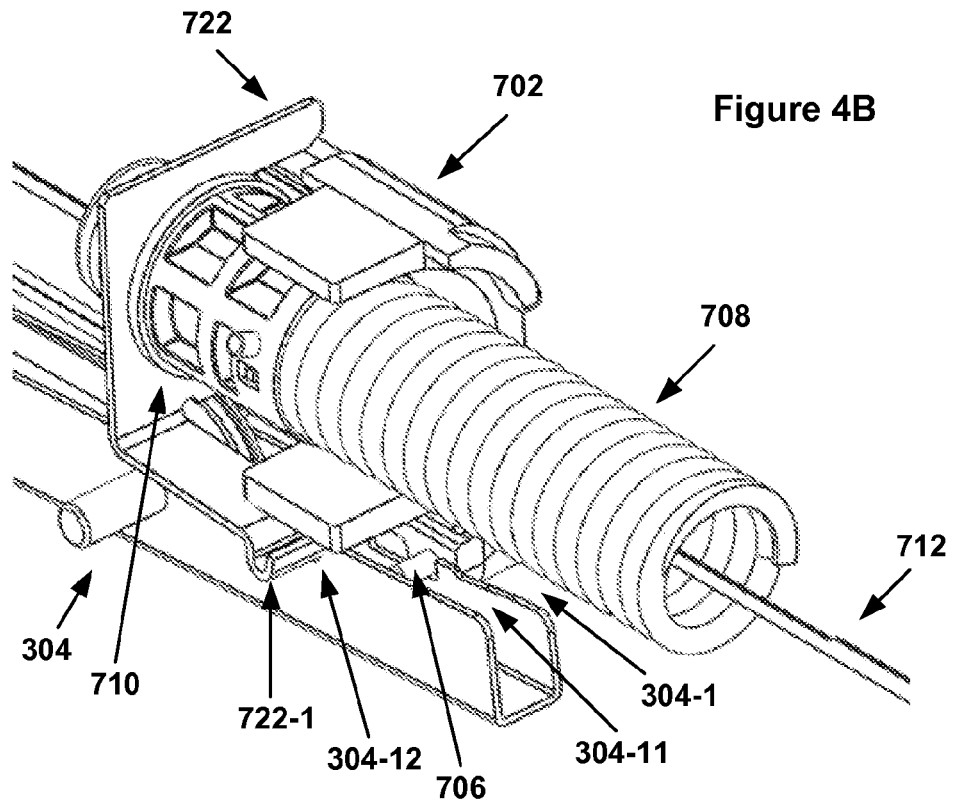
Figure 4C:
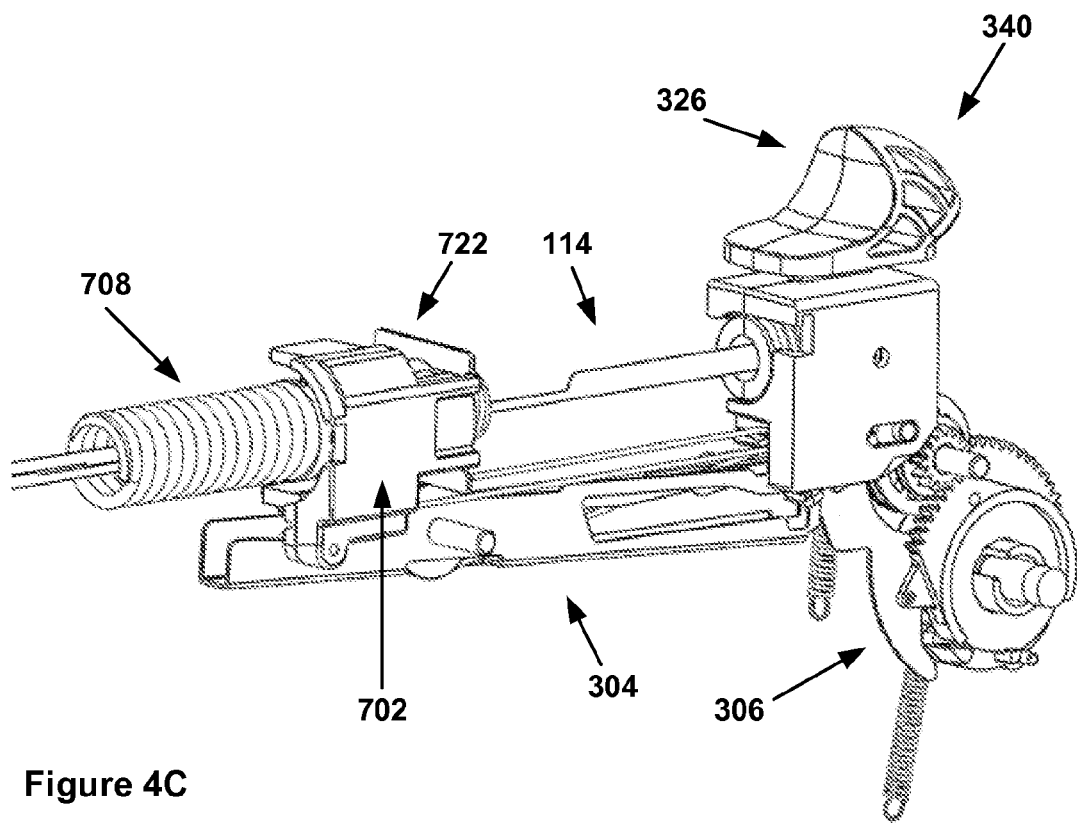
Figure 4D:
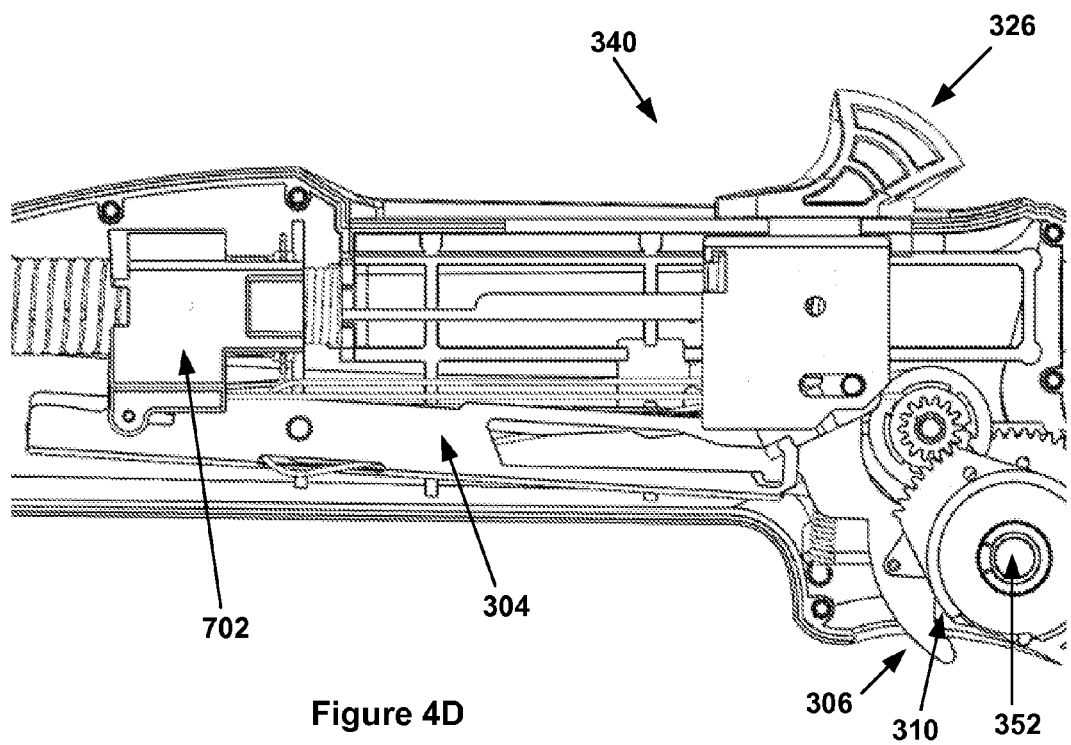

Referring back to the clamp driver 710, FIG. 3A through FIG. 3C illustrate the clamp mechanisms and the end-effector of the surgical stapling and cutting device at their activated trocar state. The compressive force may drive the clamp driver member 710 backward towards the proximal portion of the surgical device 100. The backward movement of the clamp driver member 710 pulls on the clamp strip 712, which is coupled to the jaw assembly 200 of the end-effector 106, causing the jaw assembly to close, as illustrated in FIG. 3C. As mentioned, as the clamp cable element 612 pulls the clamp slide member 702 back, the clamp slide pin 706 encounters a ramp feature 304-1 that provides positive resistance or feedback to the operating surgeon. At this stage or phase of operation, the surgeon can release the trigger element 302. The unclamp member 720 (see FIG. 3A—the unclamp member 720 may be a spring element) may provide sufficient restoration force to drive the clamp slide member 702 forward along with the clamp slide pin 706 "down" the ramp feature 304-1 (see FIG. 3B for the ramp feature 304-1). The forward movement may be translated through the clamp strip member 712 to release or open the jaw assembly 200 back to a neutral state. Alternatively, the operating surgeon can hold on to the trigger element to maintain the jaw assembly in a closed state, as illustrated in FIG. 3C. In this configuration, the surgeon can insert the end-effector 106 through an opening, a port, or a trocar to introduce the working portion of the surgical device 100 into a cavity of a patient to perform stapling and cutting of tissue at a target surgical site. In this initial closed configuration, the jaw assembly 200 may be in its smallest cross-sectional diameter or profile in which the end-effector 106 can fit through a small opening. This configuration for the jaw assembly 200 may be referred as the "trocar" mode. In addition, in this configuration, the anvil member 202 and staple channel 204 may be oriented substantially horizontally. Also, the anvil member 202 and staple channel 204 may be substantially parallel to one another in the trocar mode.

Figure 4E:
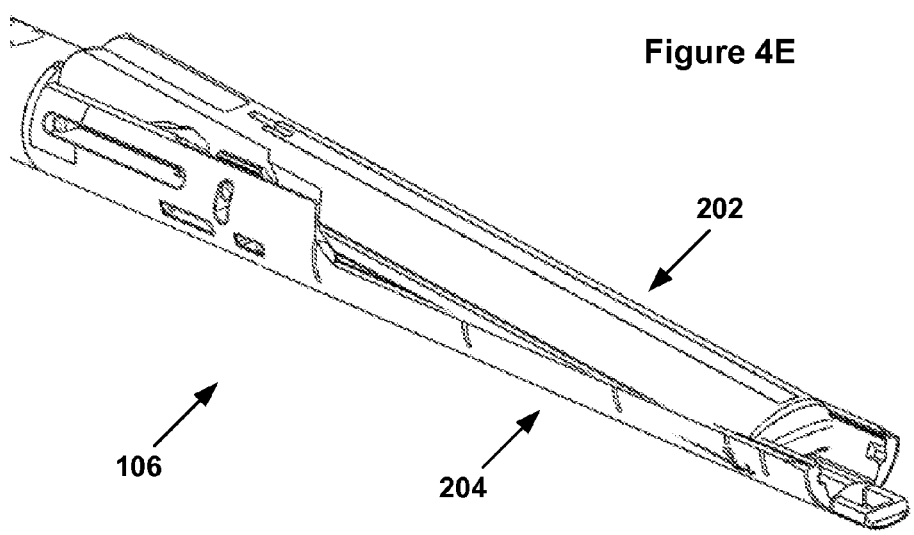
Figure 4F:
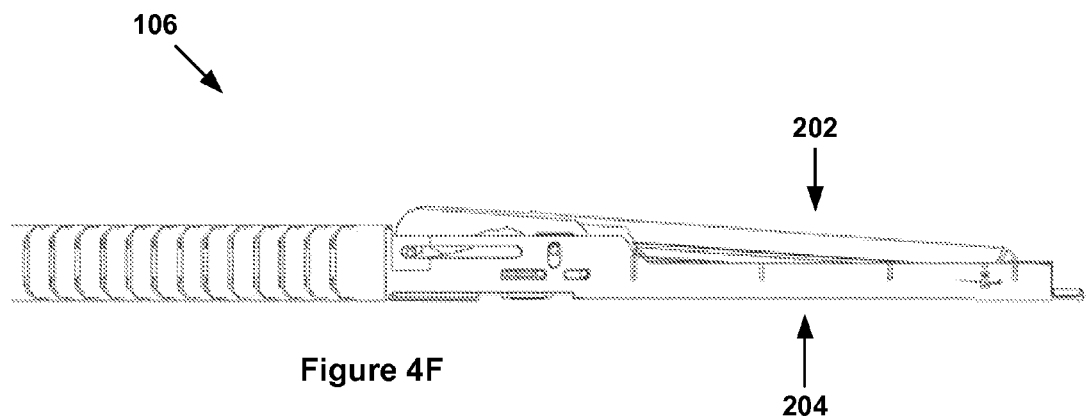

FIG. 4A through FIG. 4F illustrate the clamp mechanisms and the end-effector of the surgical stapling and cutting device at their activated clamp state. After the first activation of the clamp drive assembly 600, an additional activation of the trigger element 302 may cause the mechanisms of the clamp drive assembly 600 to tension the clamp cable member 612 to pull on the clamp slide member 702. As the clamp slide member 702 is pulled backward, the clamp slide pin element 706 is also pulled along backward into a first clamp lock pocket element or first clamp lock pocket feature 304-11. The clamp limit clip tab element 722-1 of the clamp limit clip member 722, moving substantially in concert with the clamp slide member 702 and clamp slide pin element 706, slides into or clicks into a second clamp lock pocket element or second clamp lock pocket feature 304-12. As both the clamp slide pin 706 and the clamp limit clip tab 722-1 are resting in their respective first clamp lock retainer element 304-11 and clamp lock retainer element 304-12, the jaw assembly 202 is placed into a clamp mode configuration, as illustrated in FIG. 4E and FIG. 4F. As should be noted in FIG. 4E and FIG. 4F, the proximal region of the anvil member 202 may be slightly elevated. This configuration allows the anvil member 202 to exert greater leverage in clamping a target tissue between the anvil member 202 and the channel member 204 (containing a staple cartridge or staple holder). Although not illustrated, the channel member 204 will hold a staple cartridge or staple holder for deployment of staples onto a target tissue. As such, the target tissue may be considered as being clamped between the anvil member 202 and the staple cartridge or staple holder (held by the channel member 204).

Figure 5A:
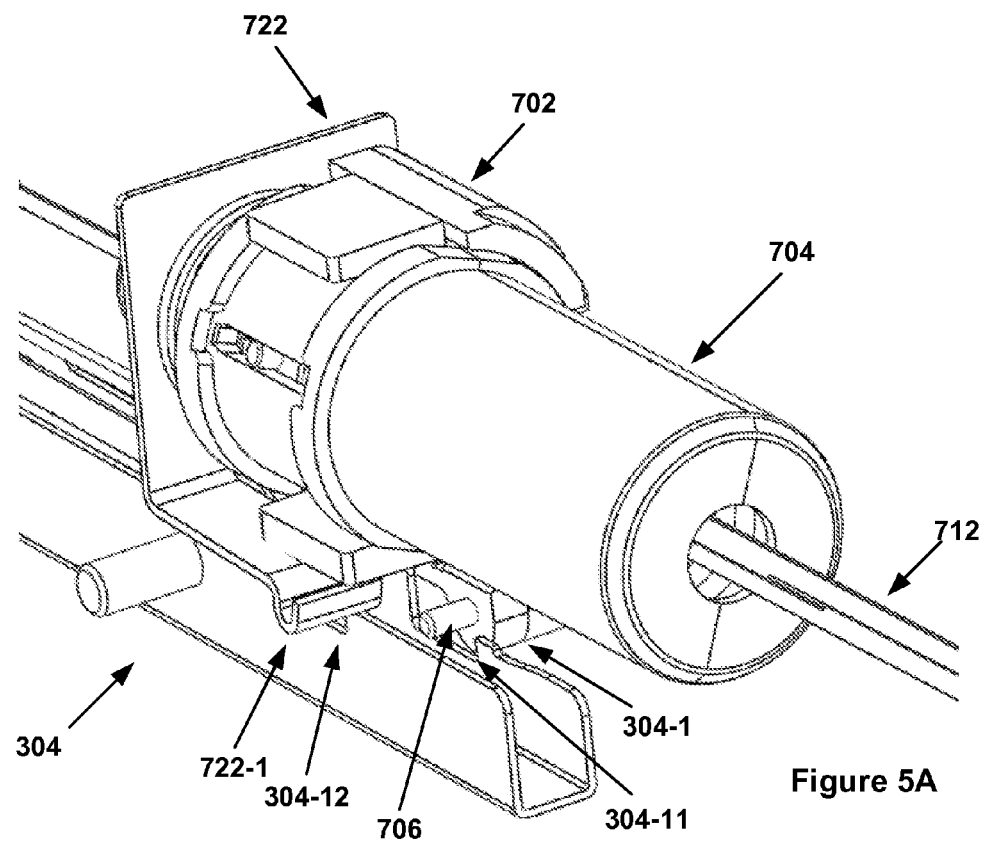
FIG. 5A through FIG. 5C illustrate the clamp mechanisms with fail-safe feature when the surgical stapling device encounters thick tissue at a target surgical site.
Figure 5B:
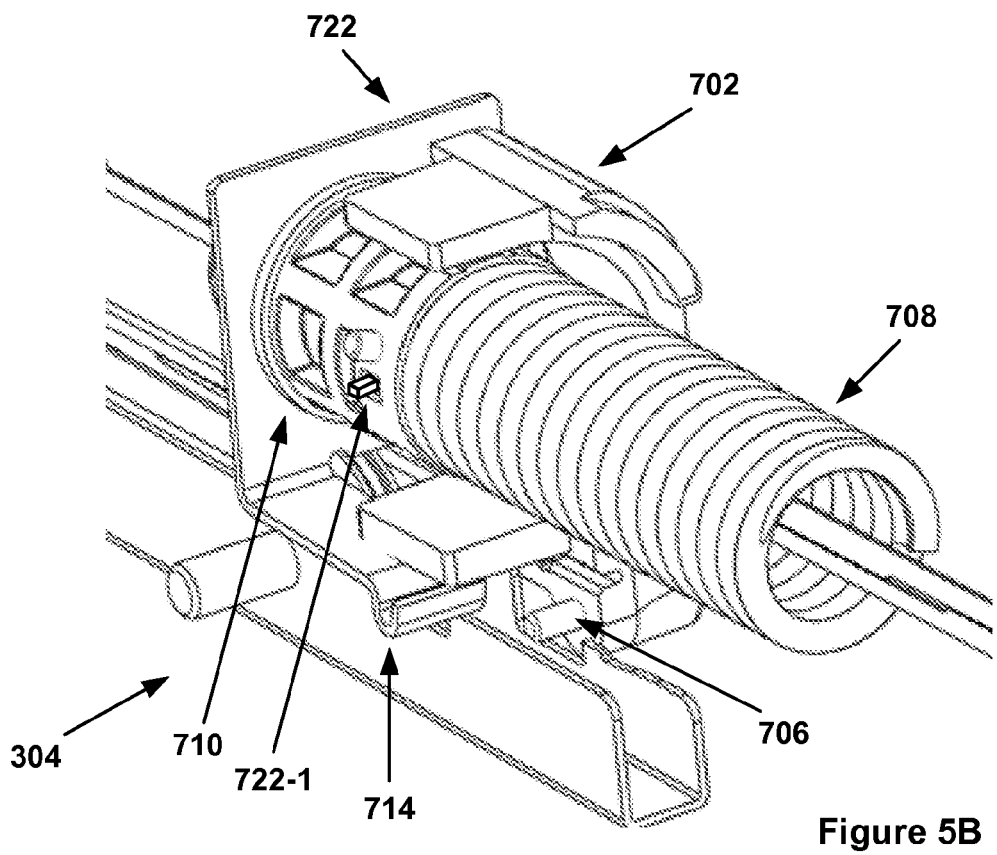
Figure 5C:
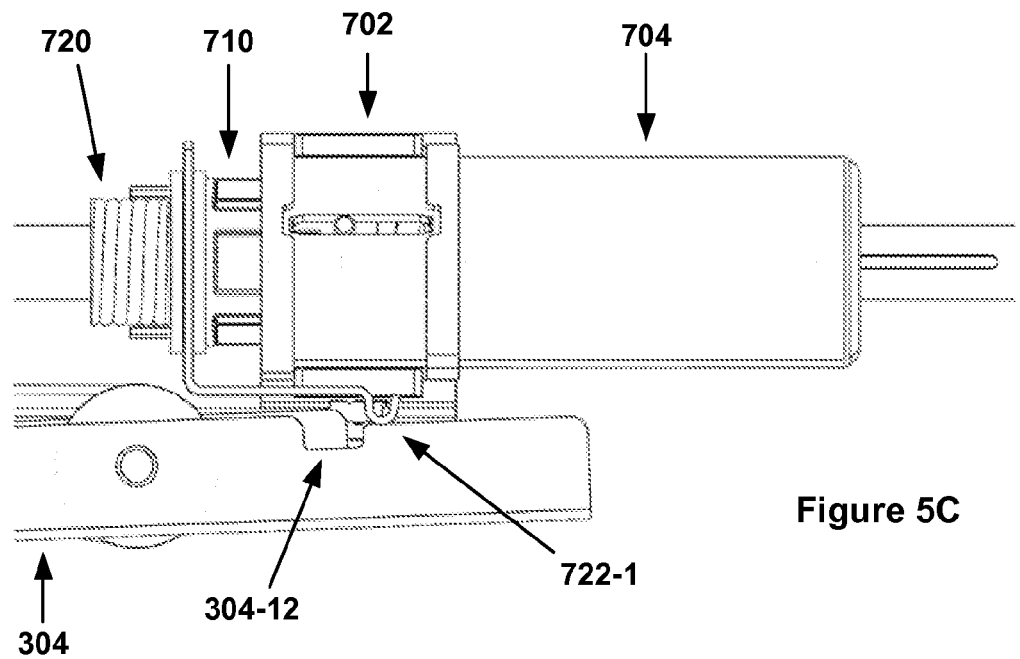

FIG. 5A through FIG. 5C illustrate the clamp mechanisms with fail-safe features to avoid malfunctions when the surgical stapling device encounters thick tissue or overly thick tissue that causes ineffective clamping and/or stapling. As illustrated in FIG. 5A, when the surgical device 100 encounters and attempts to clamp down onto thick tissue or overly thick tissue, the mechanisms of the clamp assembly 700 prevents the jaw assembly from being placed into a clamp mode, a secured clamp mode, or a locked clamp mode. As illustrated in FIG. 5A, FIG. 5B, and FIG. 5C, the clamp limit clip tab member 722-1 may be sitting on the cusp of the second clamp lock pocket feature 304-12, instead of sitting in the second clamp lock pocket element 304-12. If both the clamp slide pin member 706 and clamp limit clip member 722-1 are sitting in their respective first clamp lock retainer pocket feature 304-11 and second clamp lock retainer pocket feature 304-12, then the jaw assembly may be in a clamp lock mode. However, if the clamp limit clip tab member 722-1 is not placed into the second clamp lock retainer feature 304-12, then the jaw assembly 200 of the surgical device is not placed into a clamp mode. Instead, as the clamp cable member 612 asserts tension to pull on the clamp side member 702, the clamp spool member 704 is pulled back and exerts a compressive force onto clamp limit member 708, which may be a spring element that deforms or deflected and absorbs the compressive force. Under typical scenarios, the clamp limit member 708 is not sufficiently compressed or deflected; instead, the compressive force is transferred substantially directly to the clamp driver member 710 to drive close the jaw assembly 200 into a clamped configuration, e.g., a clamp lock mode. However, when sufficiently thick tissue or overly thick tissue is encountered, the jaw members of the jaw assembly 200 cannot clamp down sufficiently into a proper clamping configuration, even though the clamp slide member 702 is being pulled backwards to draw the jaw assembly close into a clamping configuration. In this particular scenario, the clamp limit element 708 absorbs the compressive force exerted by the clamp cable element 612. As such, even though the clamp slide member 702 is pulled back by the clamp cable member 612 and the clamp slide pin member is pulled back into the first clamp lock retainer pocket feature 304-11, the clamp driver member 710 along with the clamp limit clip member 722 do not move back. As such, correspondingly, the clamp limit clip tab element does not move back into the second clamp lock retainer pocket feature 304-12. In other words, the clamp slide member 702 can be decoupled with the clamp driver member 710. As such, the clamp slide member 702 can translate or move independently from the clamp drive member 710. As illustrated in FIG. 5A through FIG. 5C, for this example, the clamp limit clip tab element 722-1 remains on the edge or support of the clamp lock member 304. The clamp limit clip tab element 722-1 does not move into the second clamp lock retainer pocket feature 304-12.

Figure 6A:
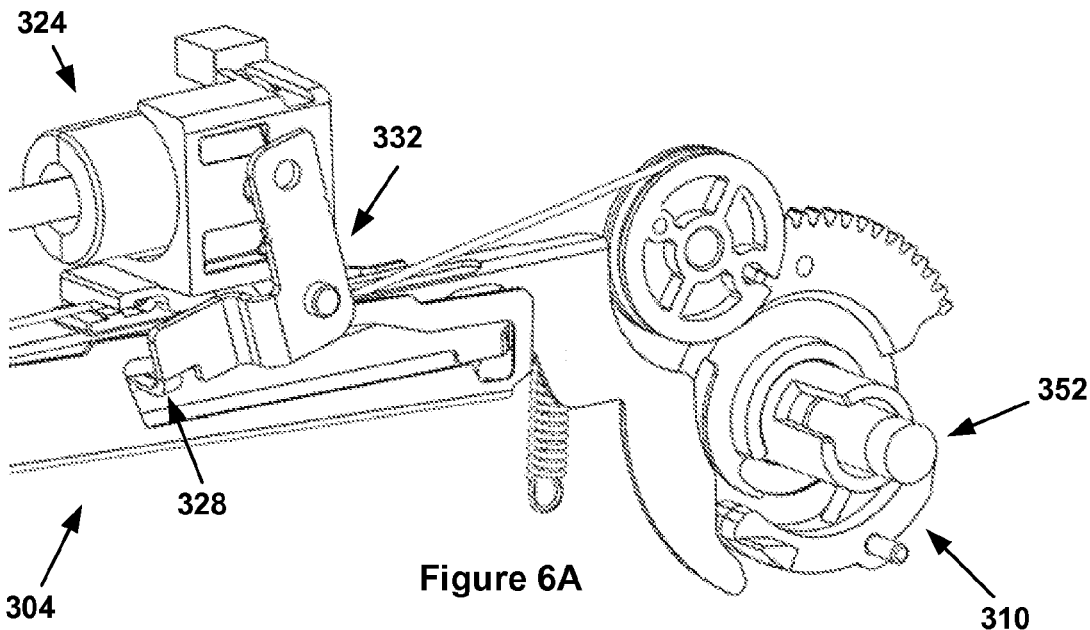
FIG. 6A through FIG. 6E illustrate the unclamp or clamp reset mechanisms of the surgical device.
Figure 6B:
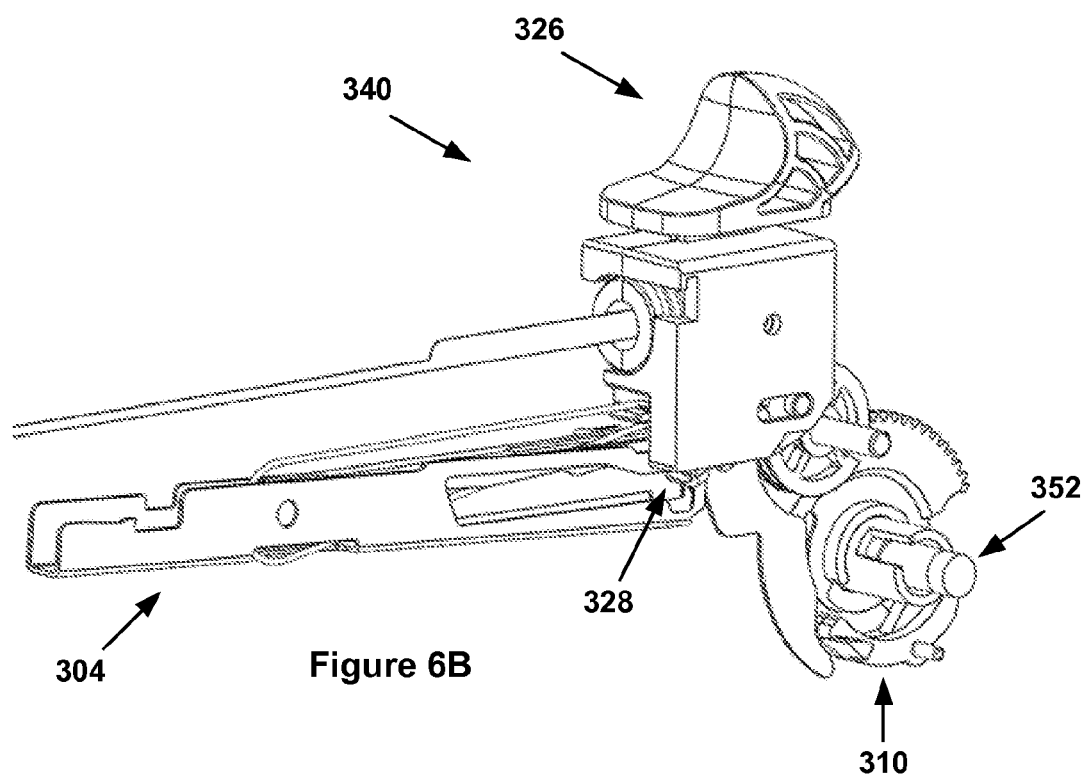
Figure 6C:
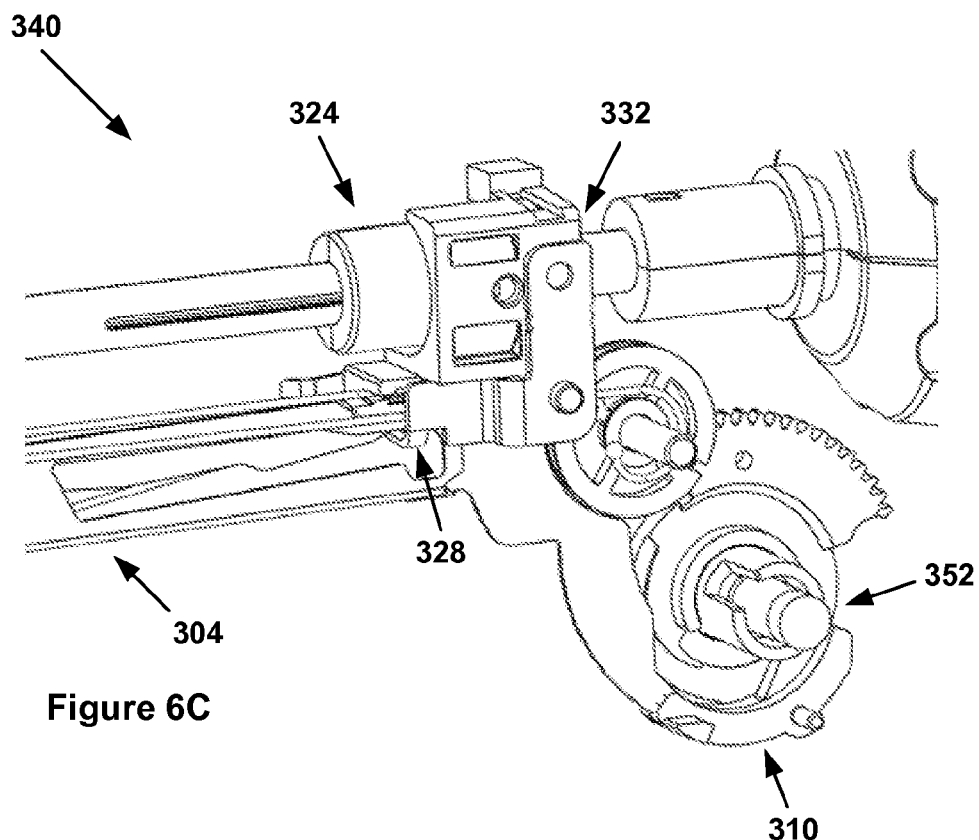
Figure 6D:
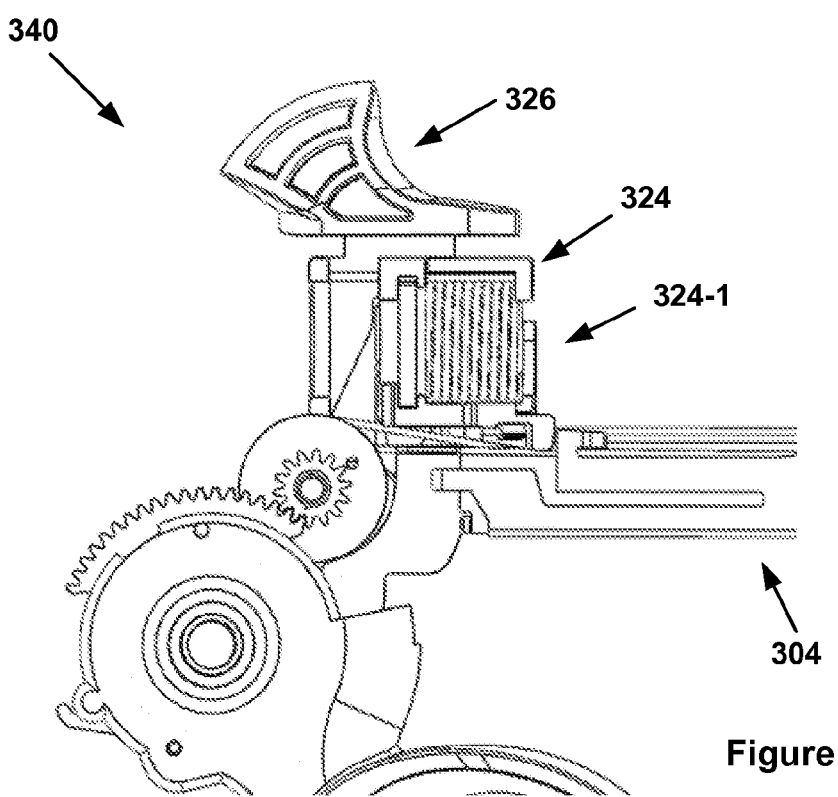
Figure 6E:
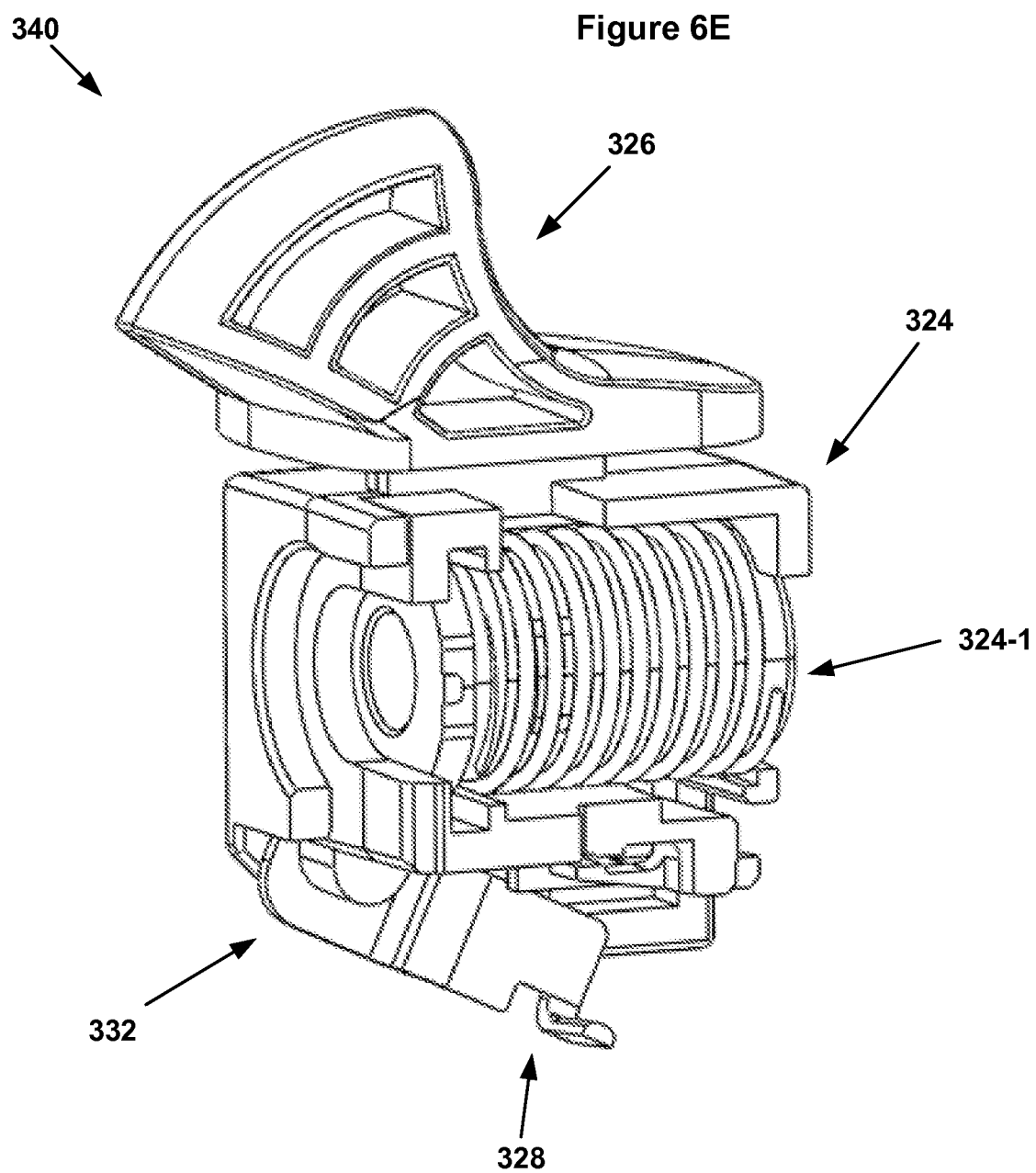

In typical operation, the jaw assembly 200 of the surgical device 100 is placed in a clamp mode, as illustrated in FIG. 4A through FIG. 4F. The clamped target tissue is ready to be stapled or stapled and cut. The next phase of operation for the surgical device 100 involves the deployment mode. That is, the mode of operation for the surgical device 100 can be switched or place into deployment mode by activating the mode switch button 352. In the deployment mode, various mechanisms are operated to deploy staples to staple a target tissue or various mechanisms are operated to deploy staples and a knife to staple and cut a target tissue at a surgical site of a patient. Once the target tissue has been stapled or stapled and cut, the jaw assembly 200 can be reset and placed into unclamp state. For example, at the end of a final deployment stroke in the deployment mode, the ratchet member 310 may be raised or reset by a bump-like feature on a deploy gear of the deployment drive assembly causing the mode switch member 352 to center or reset to place the surgical device 100 back into clamp mode. The mode switch member 352 may be spring loaded to allow for self-reset. Proceeding further, the user then pulls back on the reset switch member 326, which in turn pulls back the clamp strip 712. The clamp strip member 712 may include an I-Beam element or coupled to an I-Beam member. The I-Beam element operates to maintain a desired clamp gap between the jaw members of the jaw assembly 200 (e.g., the anvil member 202 and the staple cartridge held by the staple channel 204). Once the reset switch member 326 is back in its initial position, it can still be pulled back further, compressing a deployment spool member 324 which causes an unclamp tab element 328 of the swing arm member 332 to cam up and lift the clamp lock member 304, see FIG. 6A, FIG. 6B, and FIG. 6C. As illustrated further in FIG. 6D and FIG. 6E, the deployment spool member 324 may include a reset element 324-1 (e.g., a coil spring and the like) to allow the deployment spool unit some degrees of freedom of movement that may be separate or independent of the deployment assembly. Further, as an example, the reset switch member 326 may not be directly linked or coupled to the spool member 324. As such, the reset switch member 326 may have one or more independent degrees of movement separate from the spool member 324 and/or the deployment slide member of the deployment assembly 340. Also, the spool member 324 may include a spring element, as mentioned, to allow further movement of a portion of the deployment assembly 340 that may be independent of the deployment slide member (e.g., the reset switch member 326) or portions of the deployment assembly 340. When the clamp lock member 304 is lifted by the unclamp tab element 328, it rotates and releases the clamp slide pin 706 and clamp limit clip tab element 722-1 (e.g., released from being respectively contained or retained in the first clamp lock pocket feature 304-11 and the second clamp lock pocket feature 304-12). Because the clamp lock member 304 is no longer holding the clamp limit clip member 722 and the clamp slide pin member 706, the unclamp element 720 then drives the clamp driver member 710 and clamp slide member 702 along with the clamp spool member 704 forward into their most distal position. In turn, the clamp strip 712 is driven forward to place the jaw members of the jaw assembly into an unclamp state.

In addition, it is possible to unclamp and abort deployment after the target tissue is clamped by the jaw assembly 200. In this scenario, the attending surgeon would pull back on the reset switch member 326, compressing the deployment spool member 324 causing the unclamp tab element 328 of the swing arm member 332 to rotate and lift the clamp lock member 304, see FIG. 6C, releasing the clamp slide pin member 706 and clamp limit clip tab 722-1. The operation of abort and unclamp is substantially similar to the normal unclamp operation, except the reset switch member 326 may be in its initial undeployed position, instead of the most distal position at the end of the deployment operation.

Multiple features, aspects, and embodiments of the invention have been disclosed and described herein. Many combinations and permutations of the disclosed invention may be useful in minimally invasive surgical procedures, and the invention may be configured to support various endo-cutters and/or stapling systems. One of ordinary skill in the art having the benefit of this disclosure would appreciate that the foregoing illustrated and described features, aspects, and embodiments of the invention may be modified or altered, and it should be understood that the invention generally, as well as the specific features, aspects, and embodiments described herein, are not limited to the particular forms or methods disclosed, but also cover all modifications, equivalents and alternatives. Further, the various features and aspects of the illustrated embodiments may be incorporated into other embodiments, even if not so described herein, as will be apparent to those ordinary skilled in the art having the benefit of this disclosure.

Although particular features, aspects, and embodiments of the present invention have been shown and described, it should be understood that the above discussion is not intended to limit the present invention to these features, aspects, and embodiments. It will be obvious to those skilled in the art that various changes and modifications may be made without departing from the spirit and scope of the present invention. Thus, the present invention is intended to cover alternatives, modifications, and equivalents that may fall within the spirit and scope of the following claims and their equivalents.

What is claimed is:

1. A surgical stapling device, comprising:
   a handle assembly;
   a shaft assembly coupled to said handle assembly; and
   an end-effector coupled to said shaft assembly, said end-effector comprising a jaw assembly configured to perform clamping operations,
   wherein said handle assembly comprises a trigger member to activate a clamp drive assembly to drive the clamp assembly to cause said jaw assembly to perform clamping operations,
      wherein said clamp assembly comprises:
         a clamp limit member;
         a clamp slide member coupled to said clamp limit member and actuable to either advance in a first direction or retract in a second direction, and
      wherein said drive assembly comprises:
         a clamp driver member movably coupled to said clamp limit member,
   wherein proximal movement of said clamp driver member causes said jaw assembly to clamp and wherein distal movement of said clamp driver member causes said jaw assembly to un-clamp, and
   wherein upon application of a force to said clamp slide member above a limit associated with said claim limit member, said clamp slide member decouples from said clamp driver member.

2. The surgical stapling device of claim 1, further comprising:
   a clamp lock member to lock said clamp slide member in a first clamp lock pocket feature and a second clamp lock pocket feature to lock said clamp driver member to place said jaw assembly in a clamp lock mode.

3. The surgical stapling device of claim 2, wherein when said clamp assembly moves or translates independently of said clamp driver, said clamp driver is prevented to place said jaw assembly in a clamp lock mode.

4. The surgical stapling device of claim 1, further comprising:
   a clamp lock ramp feature on said clamp lock member to provide a positive resistance to said clamp slide member prior to locking said clamp slide member in said first clamp lock pocket feature to place said jaw assembly in said clamp lock mode.

5. The surgical stapling device of claim 1, further comprising:
   a mode switch member to selectively place the surgical stapling device in a clamping mode to operate said clamp drive assembly.

6. The surgical stapling device of claim 2, further comprising:
   a reset switch member configured to activate a swing arm member to reset said clamp lock member to release said clamp slide member from said first clamp lock pocket feature and release said clamp driver member from said second clamp lock pocket feature to reset said jaw assembly from said clamp lock mode.

7. The surgical stapling device of claim 6, wherein said swing arm member includes an unclamp tab element to engage and reset said clamp lock member.

8. The surgical stapling device of claim 1, wherein said clamp limit member is a spring.

9. The surgical stapling device of claim 1, wherein said clamp limit member translates force from said clamp slide member to said clamp driver member.

10. The surgical stapling device of claim 1, wherein said clamp driver member comprises a clamp limit clip member, said clamp limit clip member comprising a clamp limit clip tab; further comprising a clamp lock member selectively engageable by said clamp limit clip tab.

11. The surgical stapling device of claim 10, wherein said clamp lock member further comprises a clamp lock pocket feature defined in an upper surface thereof, and wherein said clamp limit clip tab sits in said clamp lock pocket feature when said jaw assembly is clamped.

12. The surgical stapling device of claim 11, wherein when said clamp limit clip tab sits in said clamp lock pocket feature, said clamp limit clip tab holds said clamp slide member substantially stationary.

13. The surgical stapling device of claim 10, wherein said clamp lock member further comprises an additional clamp lock pocket feature; wherein said clamp slide member further comprises a slide pin extending therefrom; and wherein said slide pin sits in said additional clamp lock pocket feature when said jaw assembly is clamped.

14. The surgical stapling device of claim 1, further comprising a clamp strip extending through said shaft assembly; wherein said clamp strip is coupled to said clamp driver member.

15. The surgical stapling device of claim 1, further comprising a clamp cable member connected to said clamp slide member; and wherein said handle assembly comprises a trigger; wherein actuation of said trigger causes said clamp cable member to pull said clamp slide member proximally.

16. The surgical stapling device of claim 1, wherein said claim limit member is a spring, and wherein said limit is determined by said spring.

* * * * *